(12) United States Patent
Lee

(10) Patent No.: US 9,291,577 B2
(45) Date of Patent: Mar. 22, 2016

(54) APPARATUS FOR INSPECTING GLASS SUBSTRATE

(71) Applicant: Samsung Display Co., Ltd., Yongin, Gyeonggi-Do (KR)

(72) Inventor: Jae Ho Lee, Cheonan-si (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 302 days.

(21) Appl. No.: 14/019,044

(22) Filed: Sep. 5, 2013

(65) Prior Publication Data

US 2014/0118534 A1   May 1, 2014

(30) Foreign Application Priority Data

Oct. 30, 2012  (KR) .................. 10-2012-0121476

(51) Int. Cl.
*G01T 1/02* (2006.01)
*G01N 21/958* (2006.01)
*G01N 21/896* (2006.01)

(52) U.S. Cl.
CPC ............ *G01N 21/958* (2013.01); *G01N 21/896* (2013.01)

(58) Field of Classification Search
CPC .................. G01N 21/8806; G01N 2021/8893; G01N 2021/8822
See application file for complete search history.

(56) References Cited

U.S. PATENT DOCUMENTS

| 5,493,123 | A  | * | 2/1996 | Knollenberg et al. | ........ 250/372 |
| 2013/0074549 | A1 | * | 3/2013 | Ahrens et al. | ................ 65/29.21 |

FOREIGN PATENT DOCUMENTS

| JP | 2011258274 A | * | 12/2011 |
| KR | 10-2006-0033564 A | | 4/2006 |
| KR | 10-0797571 B1 | | 1/2008 |
| KR | 10-0975645 B1 | | 8/2010 |

* cited by examiner

*Primary Examiner* — Kiho Kim
(74) *Attorney, Agent, or Firm* — Robert E. Bushnell, Esq.

(57) ABSTRACT

An apparatus for inspecting a glass substrate is provided, which comprises at least one support arm including an optical sensor that senses incident light and supporting the glass substrate, and a control portion determining whether the glass substrate and the optical sensor overlap each other or a state of the glass substrate based on characteristics of the light sensed by the optical sensor.

20 Claims, 10 Drawing Sheets

APPARATUS FOR INSPECTING GLASS SUBSTRATE

CLAIM OF PRIORITY

This application makes reference to, incorporates the same herein, and claims all benefits accruing under 35 U.S.C. §119 from an application earlier filed in the Korean Intellectual Property Office on 30 Oct. 2012 and there duly assigned Serial No. 10-2012-0121476.

BACKGROUND OF THE INVENTION

1. Field of the Invention

Embodiments of the present invention relate to an apparatus for inspecting a glass substrate, and more particularly, to an apparatus for inspecting a glass substrate by optical detection.

2. Description of the Prior Art

A glass substrate that is used to fabricate a flat panel display, such as a TFT-LCD (Thin Film Transistor-Liquid Crystal Display), a PDP (Plasma Display Panel), an EL (Electro Luminescent) device, or the like, is fabricated through a forming process for forming melted glass, which is melted in a glass melting furnace, into a flat panel, and a cutting process for cutting a glass substrate to suit a predetermined standard, and the fabricated glass substrate is transported to a machining line for a machining process.

In the above-described forming, cutting, and machining processes of the glass substrate, many defects, for example, such as size error, chipping, crack, unchampering, unbevel, over-bevel, and bevel chip, may occur on the glass substrate. Further, in a handling process for loading or transporting the glass substrate after the forming, cutting, and machining processes of the glass substrate, damage of the glass substrate may also occur.

The defects of the glass substrate may be directed to deterioration of the picture quality of the flat panel display including the glass substrate. For example, if the defect occurs on a display area of the flat panel display, the display quality of the flat panel display may be deteriorated.

Further, the glass substrate may be completely destroyed during the fabricating process of the flat panel display due to the defects. For example, in order to stick photoresist onto the glass substrate in a color filer fabricating process, a heat treatment process is performed with respect to the glass substrate at a temperature of more than 220° C. for 30 to 40 minutes in an oven. At this time, the glass substrate having the defects may be unable to endure the above-described conditions and may be completely destroyed. If the glass substrate is completely damaged and breaks into fragments, it is required to stop the heat treatment process, to cool and clean the oven, to put a new glass substrate in the oven, and to heat the oven again to restart the heat treatment process. Defects of the glass substrate thus cause waste of time and costs. Further, particles of the completely destroyed glass substrate may stick to the inside of the oven to cause continuous deterioration of the oven performance. In general, more than 40 glass substrates are simultaneously treated in the oven. If any one of the glass substrates is destroyed, the remaining glass substrates may also be affected to cause all the glass substrates put in the oven to be discarded.

SUMMARY OF THE INVENTION

In order to fabricate a high-quality flat panel display in an optimum process, it is necessary to inspect defects, which may occur on the glass substrate after the forming, cutting, and machining processes of the glass substrate, to discriminate between good-quality products and inferior products of glass substrates, and to discard the inferior products of the glass substrates in advance.

Accordingly, inspection may be performed with respect to the defects that may occur on the glass substrate using an apparatus for inspecting a glass substrate after the forming, cutting, and machining processes. In an embodiment, a glass substrate may be supported on a support portion of the apparatus for inspecting a glass substrate, and defects of the glass substrate may be inspected using optical devices such as cameras or the like.

However, it may be difficult to perform an accurate inspection on portions where the glass substrate is supported by a support portion due to interference phenomenon caused by the support portion. Further, if the glass substrate is not accurately aligned on the support portion, the inspection may be performed only on a part of the glass substrate, and the glass substrate may be damaged due to collision of the glass substrate with the apparatus for inspecting the glass substrate or other devices.

Accordingly, the present invention has been made to solve the above-mentioned problems occurring in the prior art, and one subject to be solved by the present invention is to provide an apparatus for inspecting a glass substrate, which detects defects in a portion where the glass substrate is supported by a support portion and whether the glass substrate is accurately aligned on the support portion using an optical sensor.

Additional advantages, subjects, and features of the invention will be set forth in part in the description which follows and in part will become apparent to those having ordinary skill in the art upon examination of the following or may be learned from practice of the invention.

In one aspect of the present invention, there is provided an apparatus for inspecting a glass substrate, which includes at least one support arm including an optical sensor that senses incident light and supporting the glass substrate, and a control portion determining whether the glass substrate and the optical sensor overlap each other or a state of the glass substrate based on characteristics of the light sensed by the optical sensor.

In another aspect of the present invention, there is provided an apparatus for inspecting a glass substrate, which includes at least one support arm including a support surface supporting the glass substrate and an optical sensor located on the support surface, and at least one camera imaging the glass substrate by photographing the glass substrate.

In still another aspect of the present invention, there is provided an apparatus for inspecting a glass substrate, which includes a transport portion transporting a glass substrate that is put into the transport portion to an inspection area, at least one optical sensor adjacent to the transport portion to sense incident light, and a control portion determining whether the glass substrate and the optical sensor overlap each other or a state of the glass substrate based on characteristics of the sensed light.

According to embodiments of the present invention, at least the following effects can be achieved.

That is, defects on a portion where the glass substrate is supported by the support portion of the apparatus for inspecting a glass substrate can be detected.

Further, it can be detected whether the glass substrate is accurately aligned on the support portion of the apparatus for inspecting a glass substrate.

The effects according to the present invention are not limited to the contents as exemplified above, but more various effects are described in the specification of the present invention.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE INVENTION

Figure 1:
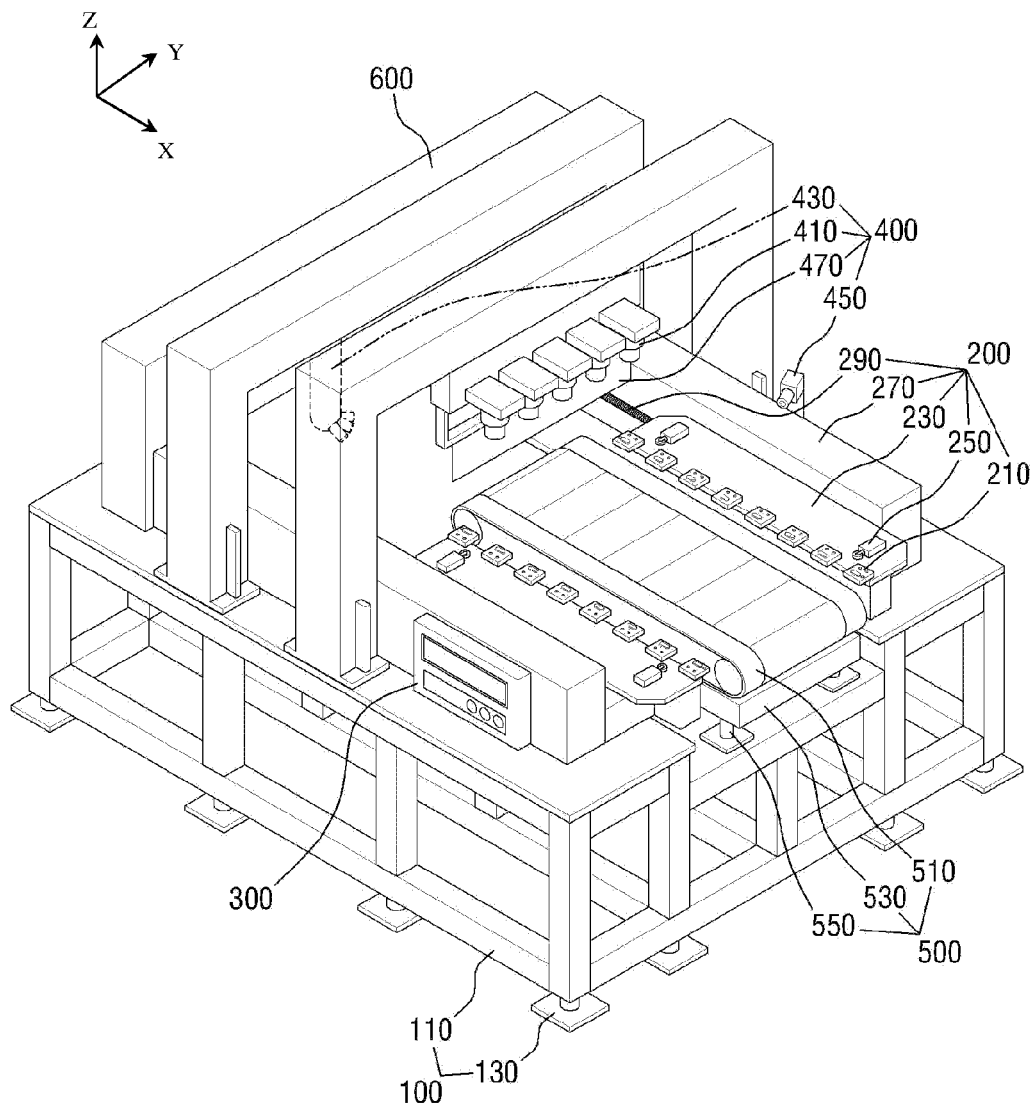
FIG. 1 is an oblique view of an apparatus for inspecting a glass substrate constructed as an embodiment according to the principles of the present invention.

The aspects and features of the present invention and methods for achieving the aspects and features will be apparent by referring to the embodiments to be described in detail with reference to the accompanying drawings. However, the present invention is not limited to the embodiments disclosed hereinafter, but can be implemented in diverse forms. The matters defined in the description, such as the detailed construction and elements, are nothing but specific details provided to assist those of ordinary skill in the art in a comprehensive understanding of the invention, and the present invention is only defined within the scope of the appended claims.

The term "on" that is used to designate that an element is on another element or located on a different layer or a layer includes both a case where an element is located directly on another element or a layer and a case where an element is located on another element via another layer or still another element. In the entire description of the present invention, the same drawing reference numerals are used for the same elements across various figures.

Although the terms "first, second, and so forth" are used to describe diverse constituent elements, such constituent elements are not limited by the terms. The terms are used only to discriminate a constituent element from other constituent elements. Accordingly, in the following description, a first constituent element may be a second constituent element.

Hereinafter, preferred embodiments of the present invention will be described in detail with reference to the accompanying drawings.

Figure 2:
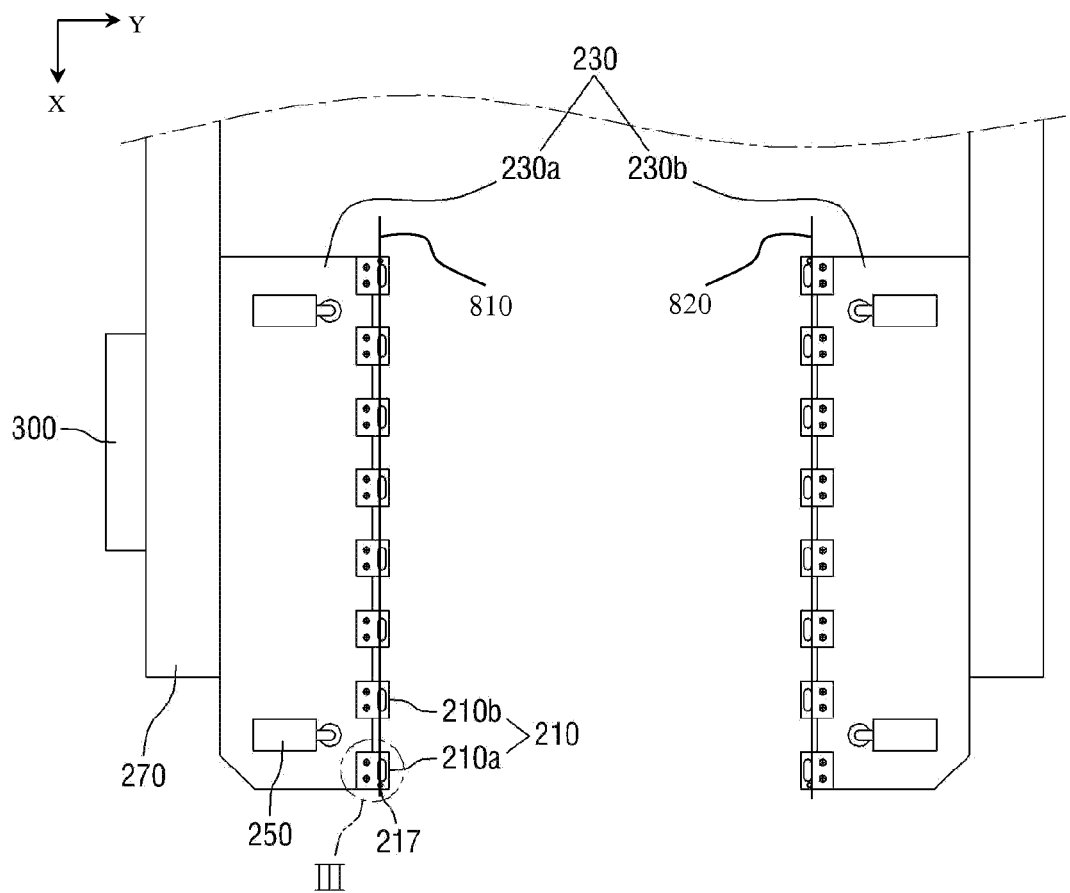
FIG. 2 is a plan view of a support portion and a control portion of an apparatus for inspecting a glass substrate constructed as an embodiment according to the principles of the present invention.
Figure 3:
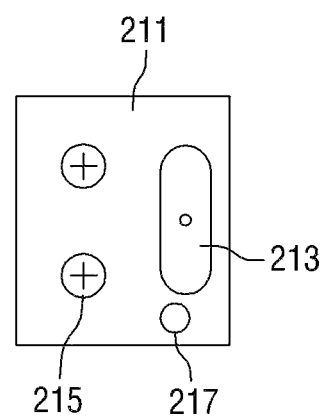
FIG. 3 is a plan view of a support arm including an optical sensor of an apparatus for inspecting a glass substrate constructed as an embodiment according to the principles of the present invention.
Figure 4:
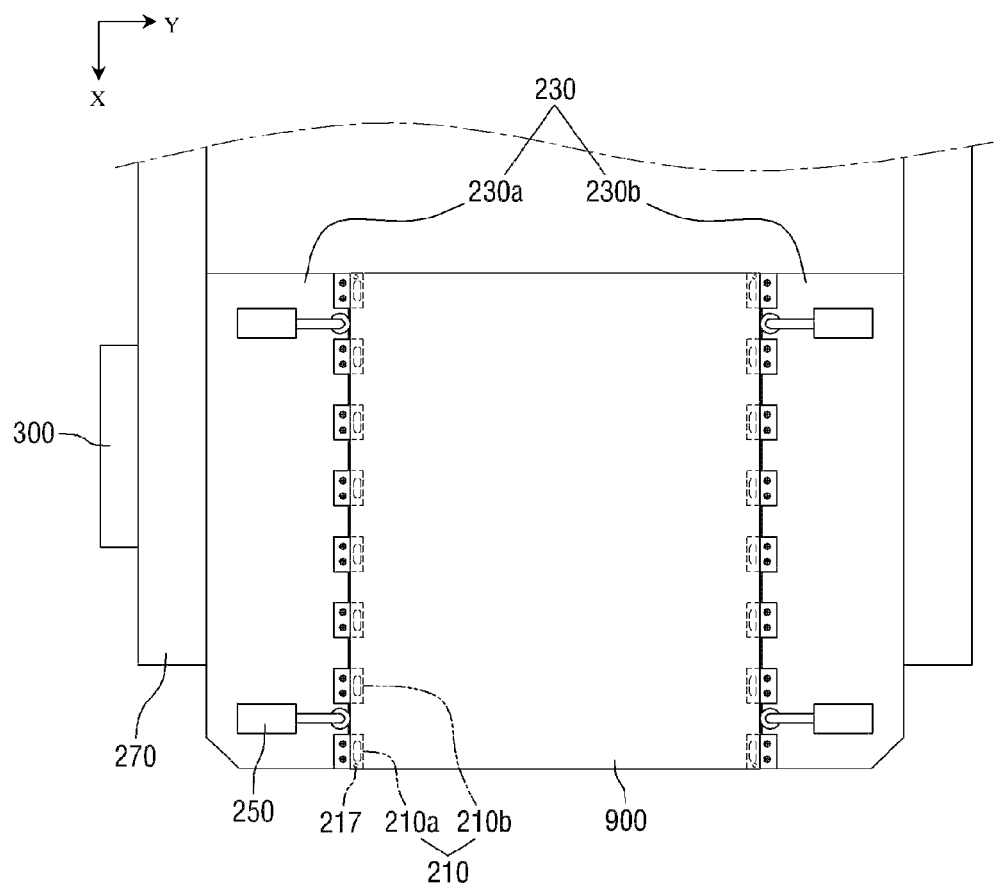
FIG. 4 is a plan view of a glass substrate, a support portion, and a control portion, which illustrates the glass substrate aligned on the support portion of an apparatus for inspecting a glass substrate constructed as an embodiment according to the principles of the present invention.
Figure 10:
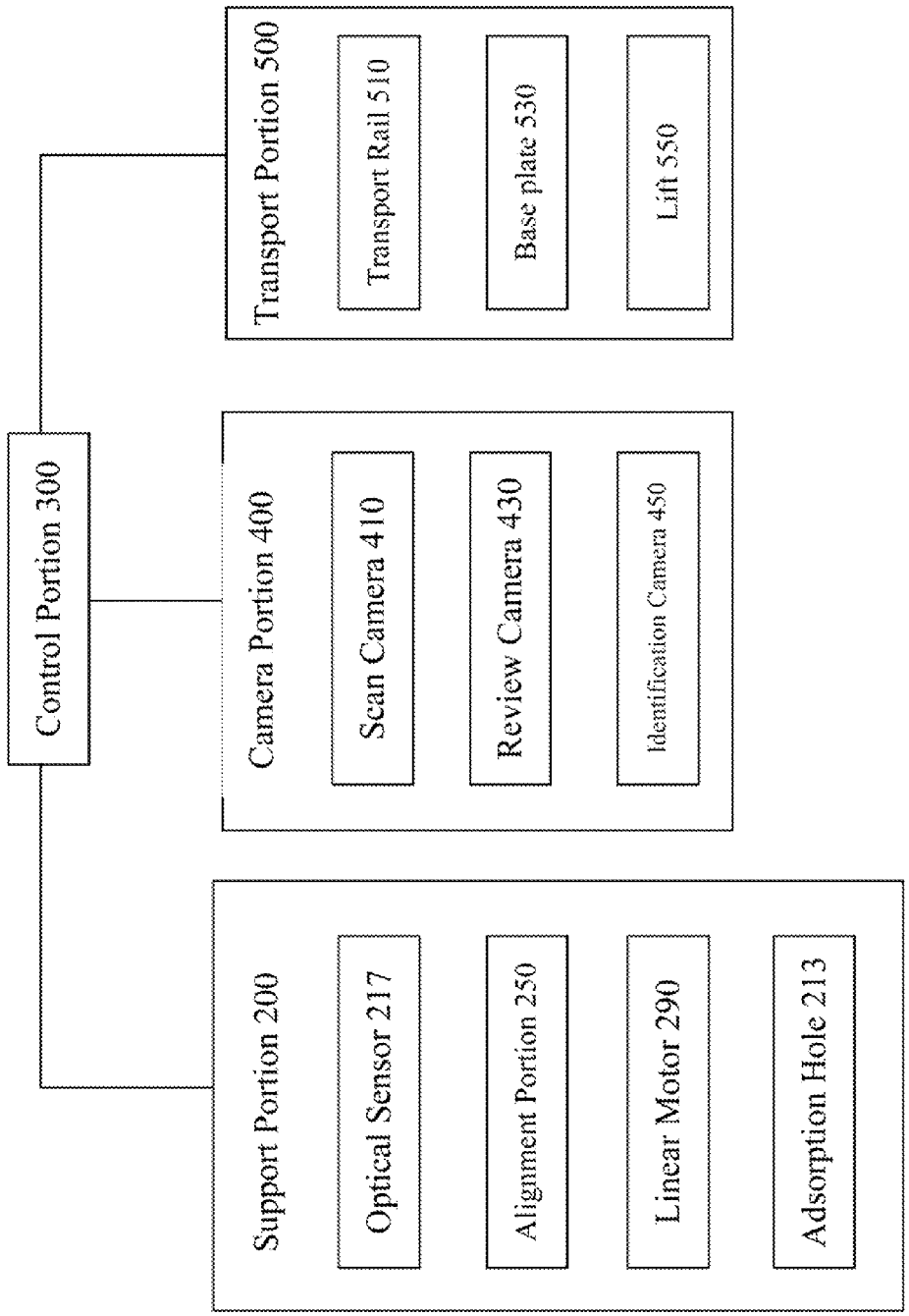
FIG. 10 is a diagram schematically showing a control of an apparatus for inspecting a glass substrate constructed as an embodiment according to the principles of the present invention.

FIG. 1 is an oblique view of an apparatus for inspecting a glass substrate constructed as an embodiment according to the principles of the present invention. FIG. 2 is a plan view of a support portion 200 and a control portion 300 of an apparatus for inspecting a glass substrate constructed as an embodiment according to the principles of the present invention, and FIG. 3 is a plan view of a support arm 210 including an optical sensor 217 of an apparatus for inspecting a glass substrate constructed as an embodiment according to the principles of the present invention. FIG. 4 is a plan view of a glass substrate 900, a support portion 200, and a control portion 300, which illustrates the glass substrate 900 aligned on the support portion 200 of an apparatus for inspecting a glass substrate constructed as an embodiment according to the principles of the present invention. FIG. 10 is a diagram schematically showing a control of an apparatus for inspecting a glass substrate constructed as an embodiment according to the principles of the present invention. Referring to FIGS. 1 through 4 and FIG. 10, an apparatus for inspecting a glass substrate includes a support arm 210 including an optical sensor 217 and a control portion 300. Further, the apparatus for inspecting a glass substrate may include a base 100, the support portion 200, a camera portion 400, a transport portion 500, and a cable box 600.

The apparatus for inspecting a glass substrate includes the optical sensor 217 for sensing incident light, and at least one support arm 210 for supporting the glass substrate 900. The detailed configuration of the support arm 210 will be described later.

The control portion 300 determines whether the glass substrate 900 and the optical sensor 210 overlap each other or the state of the glass substrate 900 based on the characteristics of light sensed by the optical sensor 217. The detailed configuration of the control portion 300 will be described later.

The base 100 may be located on a lower portion of the apparatus for inspecting a glass substrate. The base 100 may support constituent elements of the apparatus for inspecting a glass substrate except for the base 100, for example, the support portion 200, the control portion 300, the camera portion 400, the transport portion 500, and the cable box 600. The base 100 may include a base frame 110 and a load dispersion plate 130. The base frame 110 may be formed with a predetermined height from the bottom for worker's convenience, and may be made of a metal material. The load dispersion plate 130 may be designed to endure loads of the support portion 200, the control portion 300, the camera portion 400, the transport portion 500, and the cable box 600 and the load of the glass arranged on the support portion 200.

The support portion 200 may be located on the base 100. The support portion 200 may support the glass substrate 900. Further, the support portion 200 may make an inspection area enter into the glass substrate 900 to be described later. The support portion 200 may include the support arm 210, a support plate 230, an alignment portion 250, a support unit 270, and a linear motor 290.

The support arm 210 may be in contact with a lower portion of the glass substrate 900 to support the glass substrate 900. Here, the lower portion of the glass substrate 900 may be one surface of the glass substrate 900 that faces the base 100. As described above, if the support arm 210 comes in contact with the glass substrate 900, the portion where the support arm 210 and the glass substrate 900 come in contact with each other may interfere with the support arm 210, and thus an accurate inspection of the glass substrate 900 by the camera portion 400 may be difficult. However, since the edge of the glass substrate 900 may correspond to the non-display area of the flat panel display or may be hidden and surrounded by a top chassis and a bottom chassis, a precise inspection may not be required in comparison to a center portion of the glass substrate 900. Accordingly, in an embodiment of the present invention, the support arm 210 comes in contact with the edge of the glass substrate 900 to support the glass substrate 900.

Referring to FIGS. 1 and 2, a plurality of support arms 210 may be provided. The number and the arrangement form of the support arms 210 may be changed depending on the size and the shape of the glass substrate 900 supported by the support arms 210. In an exemplary embodiment, the plurality of support arms 210 may be arranged in a line. Further, two adjacent support arms 210 may be separated for a predetermined distance from each other. Here, the separation distance of the support arms 210 may be adjusted depending on the size and the shape of the glass substrate 900. That is, if three or more support arms 210 are provided, the separation distance between two adjacent support arms 210 may be equal to each other or may be different from each other. If the glass substrate 900 is in a cuboidal plate shape, one portion of the support arms 210 may be arranged in a first line 810 to come in contact with one edge of one side of the glass substrate 900 and the other portion of the support arms 210 may be arranged in a second line 820 to come in contact with the other edge of the glass substrate 900 that is spaced-apart from the edge of one side thereof. The first line 810 and the second line 820 may be separated from each other, may be parallel, and may have the same length. Further, the support arms 210 arranged in the first line 810 and the second line 820 may be symmetrical based on a space between the first line 810 and the second line 820.

The support arm 210 may include a support arm that includes the optical sensor 217 and a support arm that does not include the optical sensor 217. If the support arm 210 that includes the optical sensor 217 is defined as a first support arm 210a and the support arm 210 that does not include the optical sensor 217 is defined as a second support arm 210b, the first support arm 210a may be located at both ends of the first line 810 and at both end of the second line 820, and the second support arm 210b may be located between both ends of the first line 810 and between both ends of the second line 820. FIGS. 1 and 2 illustrate that the first support arm 210a is located at both ends of the first line 810 and at both end of the second line 820. However, the position of the first support arm 210a is not limited thereto, and the first support arm 210a may be located at one end of the first line 810 and/or at one end of the second line 820. Further, the first support arm 210a may be located between the both ends of the first line 810 and/or between the both ends of the second line 820. In an exemplary embodiment, all the support arms 210 included in the apparatus for inspecting a glass substrate may be the first support arm 210a.

The first support arm 210a may come in contact with the edge of the glass. In an exemplary embodiment, the first support arm 210a may come in contact with at least one corner portion of the glass substrate 900. In another exemplary embodiment, the first support arm 210a may come in contact with one edge and the other edge that is spaced apart from the one edge. In still another exemplary embodiment, two first support arms 210a, which have point symmetry about a weight center of the glass substrate 900, may come in contact with the edge of the glass substrate 900.

Referring to FIG. 3, the support arm 210 may include a support surface 211, an adsorption hole 213, a fastening means 215, and the optical sensor 217. The support surface 211 may be a surface that faces the lower portion of the above-described glass substrate 900. Further, the support surface 211 may be a surface that faces the camera portion 400. At least one portion of the support surface 211 may come in contact with the glass substrate 900 to support the glass substrate 900. In an exemplary embodiment, since the adsorption hole 213 adsorbs the glass substrate to fix the glass substrate 900, the portion of the support surface 211 that comes in contact with the glass substrate 900 may be a portion where the adsorption hole 213 is formed.

On the other hand, the support surface 211 may be in a rectangular shape or in a flat shape. Although FIG. 1 illustrates that the support surface 211 is flat, the shape of the support surface 211 is not limited thereto, and the support surface 211 may be concave or convex to correspond to the portion of the support surface 211 supported by the support surface 211. In an exemplary embodiment, if the portion of the glass substrate 900 supported by the support surface 211 is in a convex shape, the support surface 211 may be in a concave shape. Further, in seceding from the meaning that the terminology "support surface 211" contains, the support surface 211 may support the glass in the form of a line or dots. Further, if a plurality of support arms 210 are provided, the respective support surfaces 211 included in the plurality of support arms 210 may be located on the same plane. Although FIG. 1 illustrates that the respective support surfaces 211 included in the plurality of support arms 210 are located on the same plane, the position of the support surfaces 211 is not limited thereto, but at least two support surfaces 211 included in the plurality of support arms 210 may be located on different planes.

The adsorption hole 213 may be formed in one end portion of the support surface 211. In an exemplary embodiment, the adsorption hole 213 may be in the form of an elongated hole that is extended in one direction. Here, "one direction" may be a direction that is parallel to one edge of the support surface 211 that corresponds to one end portion of the support surface 211. Further, if the support surface 211 is in a rectangular shape, the adsorption hole 213 may be formed adjacent to one long side of the support surface 211, and the length direction of the adsorption hole 213 may be equal to the long side direction. Further, the adsorption hole 213 may be formed in a direction of a center portion of the glass substrate 900 at one end portion of the supporting surface 211. As described above, the adsorption hole 213 adsorbs the glass substrate 900 to fix the glass substrate 900.

The fastening means 215 may be formed on the other end portion of the support surface 211 that is spaced-apart from one end portion of the support surface 211 on which the adsorption hole 213 is formed. The fastening means 215 may be, for example, a bolt. At least one fastening means 215 may be provided, and in an exemplary embodiment, two fastening means may be provided. The two fastening means 215 are spaced apart from each other for a predetermined distance, and an extension line that extends the two fastening means 215 may be parallel to the other side of the support surface 211 that corresponds to the other end portion of the support surface 211. The fastening means 215 may fasten the support arm 210 and the support plate 230.

The optical sensor 217 senses light incident to the optical sensor 217. In an exemplary embodiment, the optical sensor 217 may include a light receiving portion. A light emitting portion that corresponds to the light receiving portion of the optical sensor 217 may be located on the camera portion 400 or the transport portion 500. The light emitted from the light emitting portion that is located on the camera portion 400 or the transport portion 500 may directly irradiate onto the light receiving portion of the optical sensor 217. On the other hand, if the glass substrate 900 is located on the optical sensor 217, the light may irradiate onto the light receiving portion of the optical sensor 217 after the light penetrates through the glass substrate 900. In another embodiment, the optical sensor 217 may also include the light emitting portion in addition to the light receiving portion. The light emitted from the light emitting portion of the optical sensor 217 may not irradiate onto the light receiving portion of the optical sensor 217. On the other hand, if the glass substrate 900 is located on the optical sensor 217, the light may be reflected from the glass substrate 900 and further irradiate onto the light receiving portion of the optical sensor 217.

The optical sensor 217 can sense not only the existence/nonexistence of the light incident to the optical sensor 217 but also the characteristics of the light incident to the optical sensor 217, for example, luminance, strength, or wavelength of the light. Further, if the light emitting portion emits light in a constant direction, the optical sensor 217 can sense not only whether the light irradiated from the light emitting portion is refracted but also the degree of refraction. The optical sensor 217 may correspondingly generate electrical signals representing the existence/nonexistence of and the characteristics of the light incident to the optical sensor 217. The electrical signals may be sent to the control portion 300 where the electrical signals are further processed and analyzed. A determination, for example, of whether the glass substrate 900 has passed inspection or whether a re-inspection by the apparatus or a manual re-inspection by a human should be requested, may be made by the control portion 300 based on the processed and analyzed results. The detailed operation will be described later.

The optical sensor 217 may be located on the support surface 211. In an exemplary embodiment, the light sensor 217 may be located adjacent to the adsorption hole 213. If the adsorption hole 213 is in the form of an elongated hole extended in one direction, the optical sensor 217 may be located adjacent to the end portion of the adsorption hole 213. In another exemplary embodiment, a plurality of optical sensors 217 may be provided to be located adjacent to both end portions of the adsorption hole 213. In still another exemplary embodiment, the optical sensor 217 may be formed on the inside of the adsorption hole 213. Here, the optical sensor 217 may be fixed to an inner wall of the adsorption hole 213 so as to endure the adsorption pressure when adsorbing the glass substrate 900 through the adsorption hole 213. In this configuration, the area of the support surface 211 may be saved for the adsorption hole 213 having a fixed length.

The optical sensor 217 may be formed in a dot shape. FIG. 3 illustrates that the optical sensor 217 is formed in a dot shape. However, the shape of the optical sensor 217 is not limited thereto, and the optical sensor 217 may be formed in a line or surface shape to cover the whole edge of the glass substrate 900.

The optical sensor 217 may sense the light that is incident to the optical sensor 217. In an exemplary embodiment, the optical sensor 217 may sense the light that is incident from a predetermined point on the support surface 211. In another exemplary embodiment, the optical sensor 217 can sense the light that is incident from the predetermined point on the line which is perpendicular to the support surface 211 and passes through the optical sensor 217.

The support plate 230 may support the support arms 210. As described above, the support plate 230 and the support arms 210 may be fastened by the fastening means 215. The support arms 210 may be aligned in a line on one end portion of the support plate 230. Referring to FIG. 2, a portion of the support arm 210 may be located to project from the one end portion of the support plate 230. Specifically, a portion of the support arm 210 may overlap the support plate 230. For example, the fastening means 215 may overlap the support plate 230. By contrast, another portion of the support arm 210 may not overlap the support plate 230. For example, the adsorption hole 213 and/or the optical sensor 217 may not overlap the support plate 230.

The support plate 230 may include a first support plate 230a and a second support plate 230b. The first support plate 230a and the second support plate 230b may be arranged in parallel to be spaced apart from each other. As described above, a plurality of support arms 210 may be provided, and one part of the support arms 210 may be arranged in a first line on one end portion of the first support plate 230a that faces the second support plate 230b, and the other part of the support arms 210 may be arranged in a second line on one end portion of the second support plate 230b that faces the first support plate 230a. As described above, the first line and the second line may be parallel to each other and may have the same length. Further, the first support plate 230a and the second support plate 230b may be symmetrical about a space between the first support plate 230a and the second support plate 230b.

The alignment portion 250 may be arranged on the support plate 230. At least one alignment portion 250 may be located on one support plate 230. In an exemplary embodiment, two alignment portions 250 may be located on one support plate 230, and two alignment portions 250 may be located on both end portions of the support plate 230. In an exemplary embodiment, the alignment portion 250 may be located adjacent to the first support arm 210a. The alignment portion 250 may align the glass substrate 900 in a predetermined position.

The linear motor 290 may be located on one side surface of the support unit 270. The linear motor 290 may make the support plate 230 enter into the inspection area. Here, the inspection area may mean an area where the glass substrate 900 is precisely inspected by the camera portion 400. In an exemplary embodiment, two linear motors 290 may exist, and the respective linear motors 290 are connected to the first support plate 230a and the second support plate 230b to make the first support plate 230a and the second support plate 230b enter into the inspection area simultaneously.

The support unit 270 may support the support plate 230. The support plate 230 may be connected onto one side surface of the support unit 270. In an exemplary embodiment, two support units 270 may be provided, and the respective support units 270 are connected to the first support plate 230a and the second support plate 230b to support the first support plate 230a and the second support plate 230b.

The control portion 300 may be located on the other side surface of the support unit 270. As described above, the control portion 300 determines whether the glass substrate 900 and the optical sensor 217 overlap each other or the state of the glass substrate 900 based on the characteristics of the light sensed by the optical sensor 217. More specifically, if the glass substrate 900 is located on the optical sensor 217 in a state where the optical sensor 217 is located on the support surface 211 and the optical sensor 217 senses the light incident to the optical sensor 217, the light irradiated from the light emitting portion is incident to the optical sensor 217, and in this light incident process, the characteristics of the light is changed by the glass substrate 900. In this case, the control portion 300 can determine the existence/nonexistence of the glass substrate 900 and the state of the glass substrate 900 by determining the change characteristics of the light. In an exemplary embodiment in which the optical sensor 217 includes both the light emitting portion and the light receiving portion, if the light irradiated from the light emitting portion is not incident to the light receiving portion, the control portion 300 may determine that the glass substrate 900 does not exist on the optical sensor 217. On the other hand, if the light irradiated from the light emitting portion is incident to the light receiving portion, the light incident to the light receiving portion is the light reflected from the glass substrate 900, and thus the control portion 300 determines that the glass substrate 900 exists on the optical sensor 217. Here, by further inspecting the characteristics of the light incident to the light receiving unit, for example, the light luminance or strength, the control portion 300 can determine even the state of the glass substrate 900 on the optical sensor 217.

The camera portion 400 may be located on the support portion 200. The camera portion 400 may include at least one camera. In the case where the glass substrate 900 enters into the inspection area, the camera may be located on an upper portion of the glass substrate 900. The camera portion 400 can make an image of the glass substrate 900 by photographing the glass substrate 900. The camera portion 400 may include a scan camera 410 that measures the reflectivity of the irradiated light after irradiating the light onto the glass substrate 900, a review camera 430 that is connected to a display (not shown) so as to confirm the imaged glass substrate 900 by the naked eye, and an identification camera 450 that can identify an identification code of the glass substrate 900. Further, in order to obtain a clear image of the glass substrate 900 with good picture quality, the camera portion 400 may further include reflective illumination 470 or permeable illumination (not illustrated).

The transport portion 500 may be located between the first support plate 230a and the second support plate 230b of the support portion 200. The glass substrate 900 enters into the transport portion 500, and the transport portion 500 may transport the glass substrate 900 between the first support plate 230a and the second support plate 230b or to the inspection area. The transport portion 500 may include a transport rail 510, a base plate 530, and a lift 550. The transport rail 510 comes in contact with the glass substrate 900 and transport the glass substrate between the first support plate 230a and the second support plate 230b or to the inspection area. The base plate 530 may support the transport rail 510 and drive the transport rail 510. The lift 550 may make the transport rail 510 and the base plate 530 ascend or descend. Accordingly, if the transport rail 510 transports the glass substrate 900 between the first support plate 230a and the second support plate 230b, the edge of the glass substrate 900 may overlap at least a portion of the support surface 211, and the transport portion 500 may descend to make the glass substrate 900 come in contact with the support surface 211 only.

The cable box 600 may be located on one end portion of the base 100, and perform length adjustment and custody of a cable connected to the support portion 200, the camera portion 400, and the transport portion 500.

As shown in FIG. 10, the control portion 300 may respectively send instructions to and receive information from the support portion 200, camera portion 400, and transport portion 500. More specifically, the control portion 300 may send instructions to the optical sensor 217 to sense the light incident to the optical sensor 217, sending instructions to the alignment portion 250 to align the glass substrate 900, send instructions to the linear motor 290 to move the support plate 230 into or out of the inspection area, send instructions to valves and regulators which adjust the adsorption pressure of the adsorption hole 213, send instructions to the scan camera 410 when the glass substrate 900 is ready to inspect, send instructions to the review camera 430 to monitor the inspection area or the glass substrate 900, send instructions to the identification camera 450 to capture the identification code of the glass substrate 900, and send instructions to the transport portion 500 including the transport rail 510, lift 550, and base plate 530 to transport the glass substrate 900 into the inspection area and to precisely adjust the position of glass substrate 900 for inspection. The control portion 300 may receive the information collected by the optical sensor 217, scan camera 410, and identification camera 450. The control portion 300 may also receive the status information, for example, the position information, from the alignment portion 250, linear motor 290, transport rail 510, base plate 530, and lift 550. Thus, the control portion 300 may be able to send corresponding instructions to a respective component in accordance with the information received from each component during operation. The control portion 300 may include a storage device which logs the operations of the apparatus and tracks the inspection results. A user interface may be integrated to the control portion 300 through which the operator may review the inspection results and/or change the operation parameters of the apparatus when the material properties or the size of the substrate to be inspected changes.

Referring to FIG. 4, if the glass substrate 900 is accurately aligned on the support portion 200 of the apparatus for inspecting a glass substrate according to an embodiment of the present invention, the glass substrate may be located on all the optical sensors 217. Accordingly, the control portion 300 determines that the edge of the glass substrate 900 is not damaged and that the glass substrate 900 is accurately aligned on the support portion 200. Here, whether the glass substrate 900 is accurately aligned on the support portion 200 may be determined with reference to the state of the alignment portion 250, for example, whether the alignment portion 250 is in contact with the side surface of the glass substrate 900.

Figure 5:
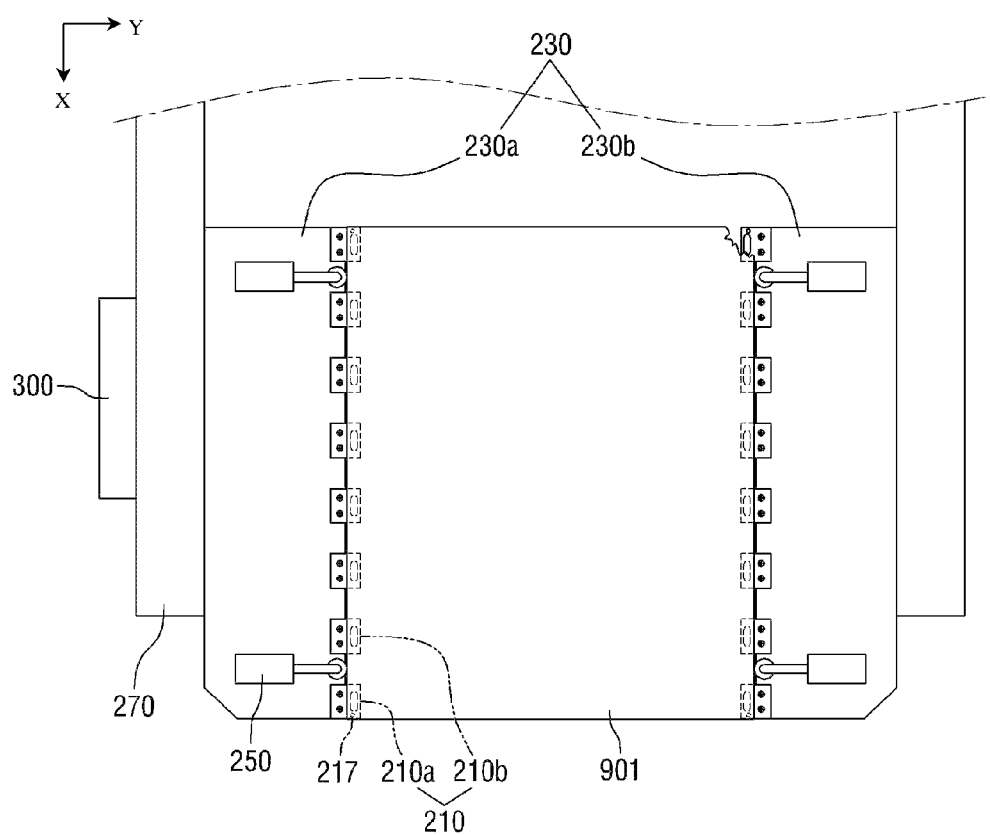
FIG. 5 is a plan view of a damaged glass substrate, a support portion, and a control portion, which illustrates the damaged glass substrate aligned on a support portion of an apparatus for inspecting a glass substrate constructed as an embodiment according to the principles of the present invention.
Figure 6:
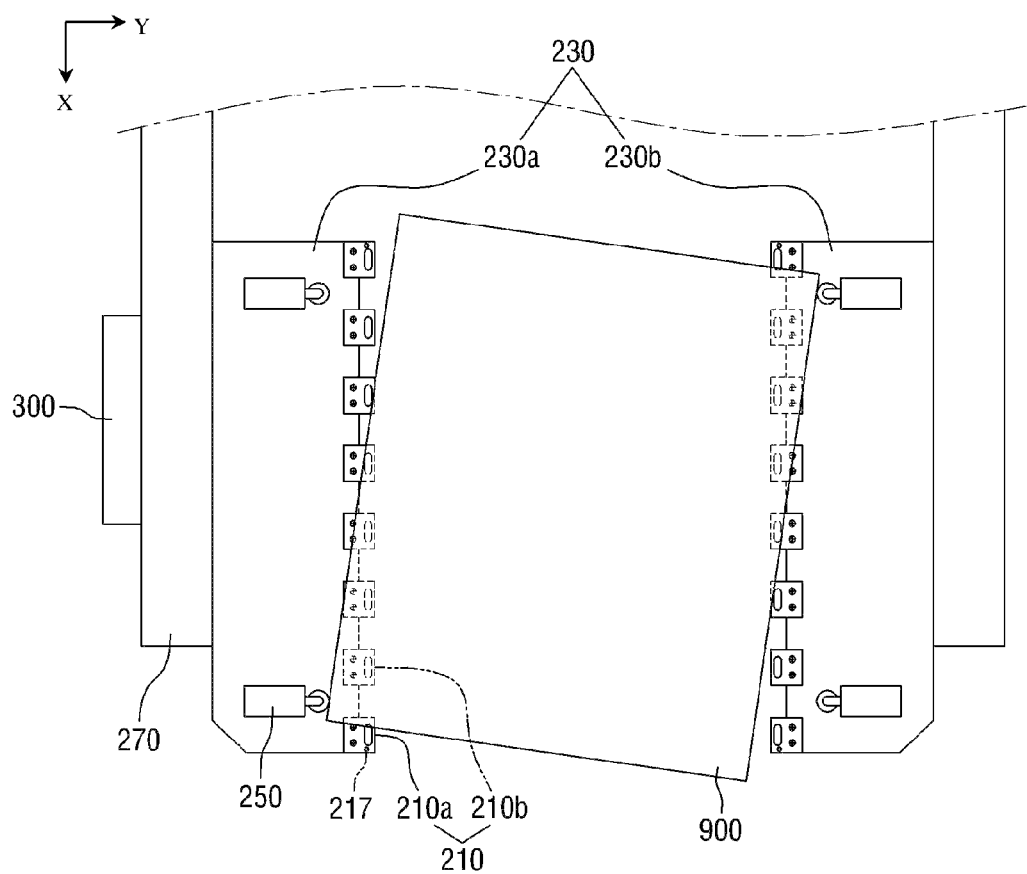
FIG. 6 is a plan view of a glass substrate, a support portion, and a control portion, which illustrates a glass substrate misaligned on a support portion of an apparatus for inspecting a glass substrate constructed as an embodiment according to the principles of the present invention.

FIG. 5 is a plan view of damaged glass substrates 901 and 900, the support portion 200, and the control portion 300, which illustrates the damaged glass substrate aligned on the support portion 200 of the apparatus for inspecting a glass substrate according to an embodiment of the present invention. FIG. 6 is a plan view of the glass substrate 900, the support portion 200, and the control portion 300, which illustrates the glass substrate 900 misaligned on the support portion 200 of the apparatus for inspecting a glass substrate according to an embodiment of the present invention.

First, referring to FIG. 5, if the damaged glass substrate 901 or 900 is accurately aligned on the support portion 200, the alignment portion 250 normally aligns the glass substrate 900, and in this case, the optical sensor 217 that corresponds to the damaged corner portion may be exposed. Accordingly, the control portion 300 may command to discard the damaged glass by determining the state of the normal alignment portion 250 and the characteristic of the light incident to the exposed optical sensor 217.

Next, referring to FIG. 6, if the glass substrate 900 is not damaged, but is not properly aligned on the support portion 200, the alignment portion 250 may perform abnormal operation and at least one optical sensor 217 may be exposed. Accordingly, the control portion 300 may determine the abnormal state of the alignment portion 250 and the characteristics of the light incident to the exposed optical sensor 217 and command to realign the glass or to ring a repair request alarm for the alignment 250.

As described above, according to the apparatus for inspecting the glass substrate according to an embodiment of the present invention, defects of a portion where the glass substrate 900 is supported by the support portion 200, for example, a portion where the glass substrate 900 and the optical sensor 217 overlap each other, and whether the glass substrate 900 is accurately aligned on the support portion 200 can be detected using the optical sensors 217.

Figure 7:
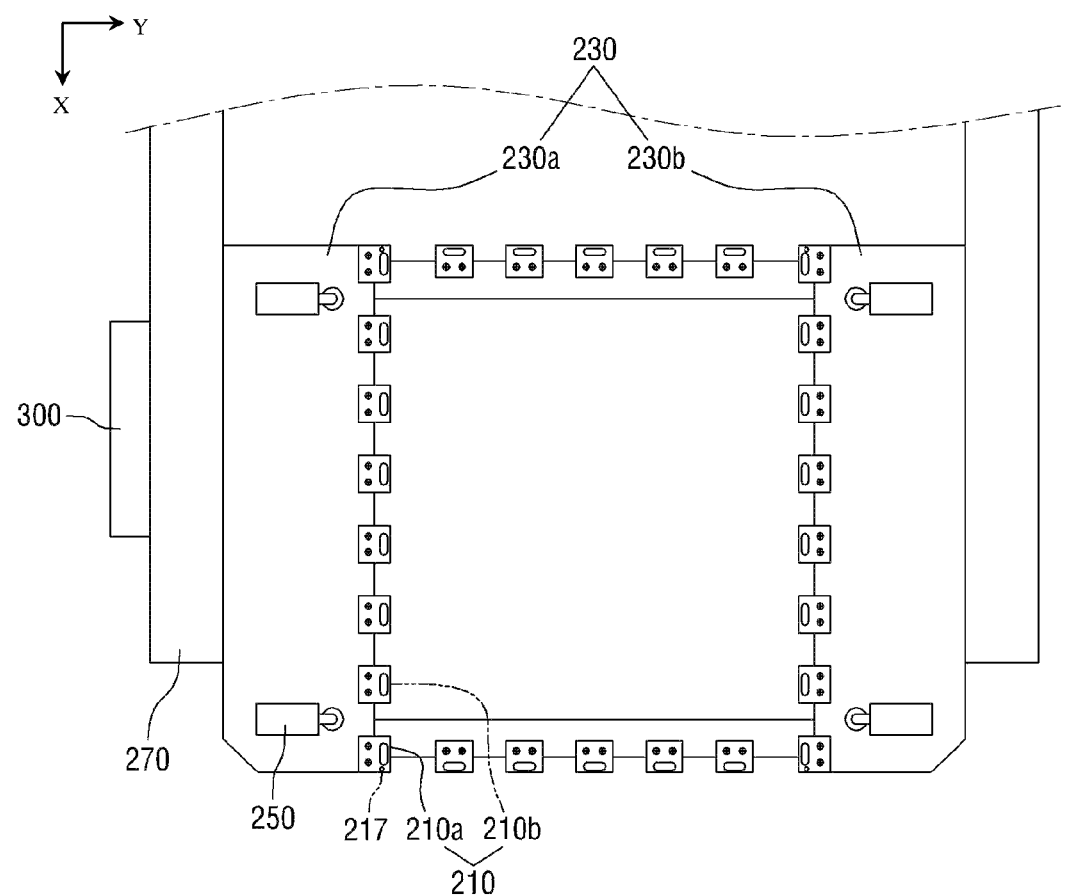
FIG. 7 is a plan view of a support portion and a control portion of an apparatus for inspecting a glass substrate constructed as another embodiment according to the principles of the present invention.

FIG. 7 is a plan view of the support portion 200 and the control portion 300 of the apparatus for inspecting a glass substrate constructed as another embodiment according to the principles of the present invention. For convenience in explanation, the same reference numerals are used for the elements substantially the same as the respective elements illustrated in FIGS. 1 to 6, and the duplicate explanation thereof will be omitted.

The apparatus for inspecting a glass substrate according to another embodiment of the present invention may further include at least one connection portion 240 that connects the first support plate 230a and the second support plate 230b. Further, the connection portion 240 may include at least one support arm 210. Here, the support arm 210 may include the first support arm 210a, or may includes both the first support arm 210a and the second support arm 210b.

The connection portion 240 may be located on the lower portion of the edge of the glass substrate 900. In an exemplary embodiment, if the glass substrate 900 is in a cuboidal plate shape, the support arms 210 on the support plate 230 may come in contact with the edge of the glass substrate 230 that corresponds to the long side of the glass substrate 900, and the support arm 210 on the connection portion 240 may come in contact with the edge of the glass substrate 900 that corresponds to the short side of the glass substrate 900.

The apparatus for inspecting a glass substrate constructed as another embodiment according to the principles of the present invention supports all edges of the glass substrate 900, and thus can stably fix the glass substrate 900 and determine whether all the edges of the glass substrate 900 are defected and whether the glass substrate 900 is accurately aligned on the support portion 200.

Figure 8:
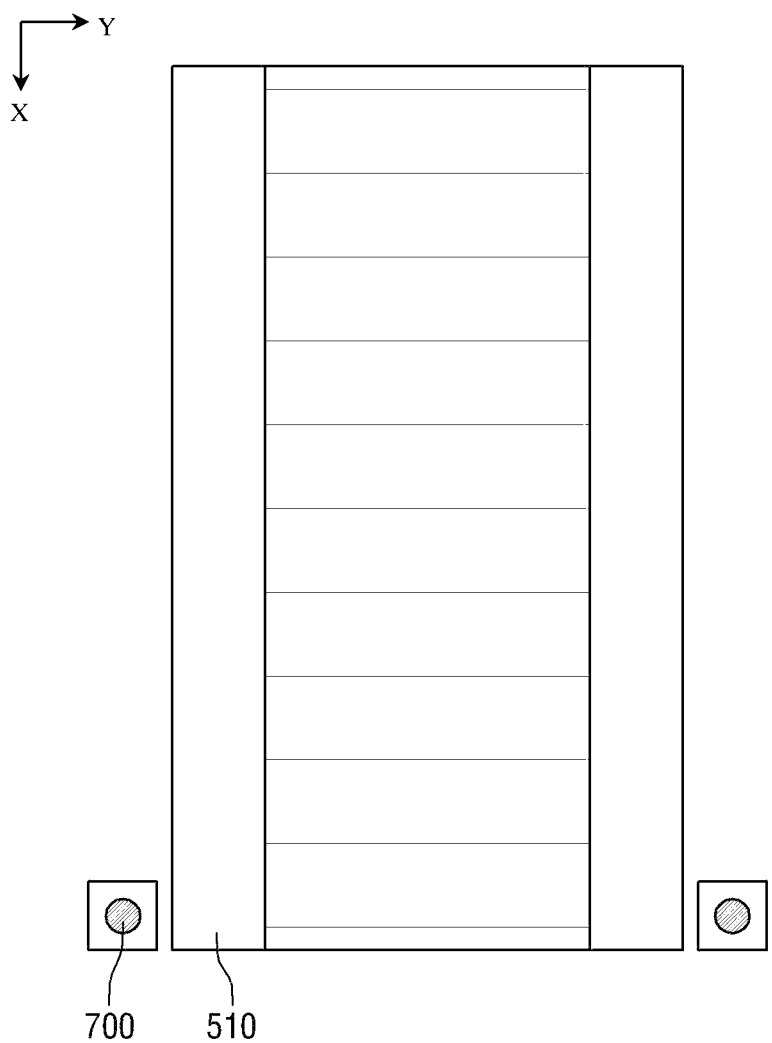
FIG. 8 is a plan view of a transport portion and an optical sensor of an apparatus for inspecting a glass substrate constructed as still another embodiment according to the principles of the present invention.
Figure 9:
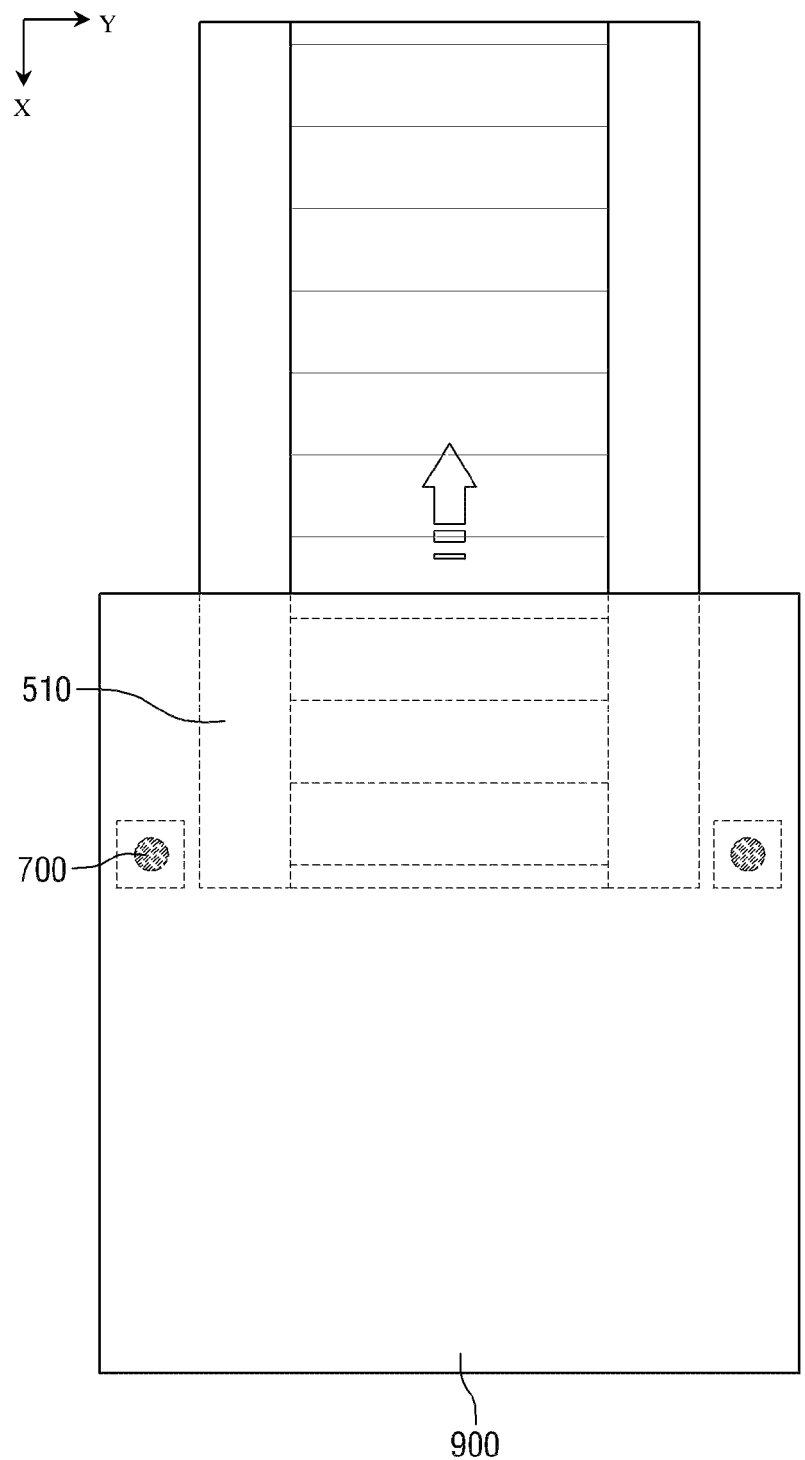
FIG. 9 is a plan view of a glass substrate, a transport portion, and an optical sensor, which illustrates the glass substrate that is transported on the transport portion of an apparatus for inspecting a glass substrate constructed as still another embodiment according to the principles of the present invention.

FIG. 8 is a plan view of the transport portion 500 and the optical sensor 700 of the apparatus for inspecting a glass substrate according to still another embodiment of the present invention. FIG. 9 is a plan view of the glass substrate 900, the transport portion 200, and the optical sensor 700, which illustrates the glass substrate 900 that is transported on the transport portion 500 of the apparatus for inspecting a glass substrate according to still another embodiment of the present invention. For convenience in explanation, the same reference numerals are used for the elements substantially the same as the respective elements illustrated in FIGS. 1 to 6, and the duplicate explanation thereof will be omitted.

Referring to FIGS. 8 and 9, the apparatus for inspecting a glass substrate constructed as still another embodiment according to the principles of the present invention includes a transport portion 500 transporting the glass substrate 900 that is loaded into the transport portion 500 to the inspection area, at least one optical sensor 700 adjacent to the transport portion 500 to sense the incident light, and a control portion 300 determining whether the glass substrate 900 and the optical sensor 700 overlap each other or the state of the glass substrate 900 based on the characteristics of the sensed light. The optical sensor 700 may be located in the path where the glass substrate 900 is loaded. Further, the optical sensor 700 may be located on the lower portion of the edge of the glass substrate 900 when the transport portion 500 transports the glass substrate 900 to the inspection area. Further, a pair of optical sensors 700 may be provided, and the pair of optical sensors 700 may be located to face both side portions of the transport portion 500.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. An apparatus for inspecting a glass substrate, comprising:
    at least one support arm supporting the glass substrate and including an optical sensor that senses light incident to the optical sensor and correspondingly generates electrical signals; and
    a control part receiving the electrical signals from the optical sensor and determining whether the glass substrate and the optical sensor overlap each other or a state of the glass substrate, based on the electrical signals representing characteristics of the sensed light.

2. The apparatus for inspecting a glass substrate of claim 1, wherein the support arm includes a support surface,
    at least a portion of the support surface comes in contact with the glass substrate, and
    the optical sensor is located on the support surface.

3. The apparatus for inspecting a glass substrate of claim 2, wherein the optical sensor comprises:
    a light emitting unit emitting light; and
    a light receiving unit sensing light incident to the light receiving unit.

4. The apparatus for inspecting a glass substrate of claim 2, wherein the support arm includes an adsorption hole that adsorbs the glass substrate onto one end portion of the support surface, and
    the optical sensor is located adjacent to the adsorption hole.

5. The apparatus for inspecting a glass substrate of claim 4, wherein the absorption hole is in the form of an elongated hole extended in one direction, and
    the optical sensor is located adjacent to an end portion in the one direction of the adsorption hole.

6. The apparatus for inspecting a glass substrate of claim 1, wherein the support arm comes in contact with an edge of the glass substrate.

7. The apparatus for inspecting a glass substrate of claim 6, wherein the support arm comes in contact with at least one corner portion of the glass substrate.

8. The apparatus for inspecting a glass substrate of claim 6, further comprising:
    a first support plate; and
    a second support plate arranged in parallel to be spaced apart from the first support plate, wherein a plurality of support arms are provided in a first line arranged on an end portion of the first support plate that faces the second support plate and in a second line arranged on an end portion of the second support plate that faces the first support plate.

9. The apparatus for inspecting a glass substrate of claim 8, wherein the first line and the second line are parallel to each other.

10. The apparatus for inspecting as glass substrate of claim 8, further comprising at least one connection portion connecting the first support plate and the second support plate to each other,
   wherein the connection portion includes the at least one support arm.

11. The apparatus for inspecting a glass substrate of claim 8, wherein the first support plate or the second support plate includes an alignment portion aligning the glass substrate in a predetermined position.

12. An apparatus for inspecting a glass substrate, comprising:
   at least one support arm including a support surface supporting the glass substrate and an optical sensor located on the support surface; and
   at least one camera imaging the glass substrate by photographing the glass substrate.

13. The apparatus for inspecting a glass substrate of claim 12, wherein the optical sensor senses the light incident to the optical sensor and correspondingly generates electrical signals, and
   the apparatus further comprises a control part receiving the electrical signals from the optical sensor and determining whether the glass substrate and the optical sensor overlap each other or a state of the glass substrate based on the electrical signals representing characteristics of the sensed light.

14. The apparatus for inspecting a glass substrate of claim 13, wherein the support arm includes an adsorption hole that adsorbs the glass substrate onto one end portion of the support surface, and
   the optical sensor is located adjacent to the adsorption hole.

15. The apparatus for inspecting a glass substrate of claim 12, wherein at least a portion of the support surface comes in contact with an edge of the glass substrate.

16. The apparatus for inspecting a glass substrate of claim 15, further comprising:
   a first support plate; and
   a second support plate arranged in parallel to be spaced apart from the first support plate,
   wherein a plurality of support arms are provided in a first line arranged on an end portion of the first support plate that faces the second support plate and in a second line arranged on an end portion of the second support plate that faces the first support plate.

17. An apparatus for inspecting a glass substrate, comprising:
   a transport portion transporting a glass substrate loaded onto the transport portion to an inspection area;
   at least one optical sensor adjacent to the transport portion sensing light incident to the optical sensor and correspondingly generating electrical signals; and
   a control part receiving the electrical signals from the optical sensor and determining whether the glass substrate and the optical sensor overlap each other or a state of the glass substrate based on the electrical signals representing characteristics of the sensed light.

18. The apparatus for inspecting a glass substrate of claim 17, wherein the optical sensor is located in a path where the glass substrate is loaded.

19. The apparatus for inspecting, a glass substrate of claim 8, wherein a pair of optical sensors are provided, and
   the pair of optical sensors are located at opposite sides of the transport portion.

20. The apparatus for inspecting a glass substrate of claim 17, wherein the optical sensor is located at a lower portion of an edge of the glass substrate when the transport portion transports the glass substrate to the inspection area.

* * * * *